(12) United States Patent　　　　(10) Patent No.:　US 12,611,234 B2
McClintock　　　　　　　　　　　　 (45) Date of Patent: 　　Apr. 28, 2026

(54) SPINAL FIXATION SYSTEM

(71) Applicant: VB Spine US Opco LLC, Leesburg, VA (US)

(72) Inventor: Larry E. McClintock, Gore, VA (US)

(73) Assignee: VB Spine US Opco LLC, Leesburg, VA (US)

( * ) Notice: Subject to any disclaimer, the term of this patent is extended or adjusted under 35 U.S.C. 154(b) by 203 days.

(21) Appl. No.: 18/142,794

(22) Filed: May 3, 2023

(65) Prior Publication Data

US 2023/0355280 A1　　Nov. 9, 2023

Related U.S. Application Data

(60) Provisional application No. 63/338,116, filed on May 4, 2022.

(51) Int. Cl.
*A61B 17/70*　　　　(2006.01)
(52) U.S. Cl.
CPC ...... *A61B 17/7035* (2013.01); *A61B 17/7032* (2013.01)
(58) Field of Classification Search
CPC .................................... A61B 17/7032–17/704
See application file for complete search history.

(56) References Cited

U.S. PATENT DOCUMENTS

| | | |
|---|---|---|
| 5,116,336 A | 5/1992 | Frigg |
| 5,360,431 A | 11/1994 | Puno et al. |

| | | |
|---|---|---|
| 5,443,467 A | 8/1995 | Biedermann et al. |
| 5,443,509 A | 8/1995 | Boucher et al. |
| 5,466,237 A | 11/1995 | Byrd, III et al. |
| 5,474,555 A | 12/1995 | Puno et al. |
| 5,476,464 A | 12/1995 | Metz-Stavenhagen et al. |
| 5,549,608 A | 8/1996 | Errico et al. |
| 5,554,157 A | 9/1996 | Errico et al. |
| 5,584,834 A | 12/1996 | Errico et al. |
| 5,586,984 A | 12/1996 | Errico et al. |

(Continued)

FOREIGN PATENT DOCUMENTS

| | | |
|---|---|---|
| EP | 1634537 A1 | 3/2006 |
| EP | 1774919 A1 | 4/2007 |

(Continued)

OTHER PUBLICATIONS

Extended European Search Report issued in Appln. No. 23171529.3 dated Oct. 25, 2023 (3 pages).

(Continued)

*Primary Examiner* — Julianna N Harvey
(74) *Attorney, Agent, or Firm* — Lerner David LLP

(57) ABSTRACT

The present disclosure is directed to a polyaxial pedicle screw including a housing, a friction plug, an anvil, a bone screw member, and a compression ring or cap. The housing includes opposing arms, a collar at a bottom portion of the housing, a cutout, and a passage. The anvil is positioned in the passage. The bone screw member includes a head and a threaded shaft extending from the head along a shaft axis, wherein the head is configured to be positioned in the passage. The friction plug is positioned in the cutout, wherein the friction plug applies a force to the head. The compression ring or cap is positioned over the collar and the friction plug.

15 Claims, 17 Drawing Sheets

(56) References Cited

U.S. PATENT DOCUMENTS

| | | | |
|---|---|---|---|
| 5,647,873 | A | 7/1997 | Errico et al. |
| 5,669,911 | A | 9/1997 | Errico et al. |
| 5,672,176 | A | 9/1997 | Biedermann et al. |
| 5,690,630 | A | 11/1997 | Errico et al. |
| 5,733,285 | A | 3/1998 | Errico et al. |
| 5,733,286 | A | 3/1998 | Errico et al. |
| 5,797,911 | A | 8/1998 | Sherman et al. |
| 5,817,094 | A | 10/1998 | Errico et al. |
| 5,863,293 | A | 1/1999 | Richelsoph |
| 5,885,286 | A | 3/1999 | Sherman et al. |
| 5,964,760 | A | 10/1999 | Richelsoph |
| 6,010,503 | A | 1/2000 | Richelsoph et al. |
| 6,074,391 | A | 6/2000 | Metz-Stavenhagen et al. |
| 6,090,110 | A | 7/2000 | Metz-Stavenhagen |
| 6,113,601 | A | 9/2000 | Tatar |
| 6,261,287 | B1 | 7/2001 | Metz-Stavenhagen |
| 6,273,888 | B1 | 8/2001 | Justis |
| 6,280,442 | B1 | 8/2001 | Barker et al. |
| 6,296,642 | B1 | 10/2001 | Morrison et al. |
| 6,355,040 | B1 | 3/2002 | Richelsoph et al. |
| RE37,665 | E | 4/2002 | Ralph et al. |
| 6,485,491 | B1 | 11/2002 | Farris et al. |
| 6,537,276 | B2 | 3/2003 | Metz-Stavenhagen |
| 6,660,004 | B2 | 12/2003 | Barker et al. |
| 6,726,689 | B2 | 4/2004 | Jackson |
| 6,869,433 | B2 | 3/2005 | Glascott |
| RE39,089 | E | 5/2006 | Ralph et al. |
| 7,087,057 | B2 | 8/2006 | Konieczynski et al. |
| 7,128,743 | B2 | 10/2006 | Metz-Stavenhagen |
| 7,211,086 | B2 | 5/2007 | Biedermann et al. |
| 7,223,268 | B2 | 5/2007 | Biedermann |
| 7,591,839 | B2 | 9/2009 | Biedermann et al. |
| 7,695,497 | B2 | 4/2010 | Cordaro et al. |
| 7,749,258 | B2 | 7/2010 | Biedermann et al. |
| 7,867,258 | B2 | 1/2011 | Drewry et al. |
| 7,947,065 | B2 | 5/2011 | Hammill, Sr. et al. |
| 7,951,172 | B2 | 5/2011 | Chao et al. |
| 8,012,188 | B2 | 9/2011 | Melkent et al. |
| 8,403,971 | B2 | 3/2013 | Barrus et al. |
| 8,430,914 | B2 | 4/2013 | Spratt et al. |
| 8,506,601 | B2 | 8/2013 | Gephart et al. |
| 8,556,938 | B2 | 10/2013 | Jackson et al. |
| 8,814,919 | B2 | 8/2014 | Barrus et al. |
| 8,882,817 | B2 | 11/2014 | Jones et al. |
| 9,393,049 | B2 | 7/2016 | Jones et al. |
| 9,451,993 | B2 | 9/2016 | Jackson |
| 9,453,526 | B2 | 9/2016 | Black et al. |
| 9,924,971 | B2 | 3/2018 | Biedermann et al. |
| 9,924,973 | B2 | 3/2018 | Jones et al. |
| 10,499,957 | B2 | 12/2019 | Jones et al. |
| 10,610,265 | B1 * | 4/2020 | Ark .................. A61B 17/7052 |
| 10,716,609 | B2 | 7/2020 | Biedermann et al. |
| 2002/0026193 | A1 | 2/2002 | Barker et al. |
| 2003/0004512 | A1 | 1/2003 | Farris et al. |
| 2003/0125741 | A1 | 7/2003 | Biedermann et al. |
| 2005/0192571 | A1 | 9/2005 | Abdelgany |
| 2005/0277928 | A1 | 12/2005 | Boschert |
| 2006/0074419 | A1 | 4/2006 | Taylor et al. |
| 2006/0111715 | A1 | 5/2006 | Jackson |
| 2006/0149235 | A1 | 7/2006 | Jackson |
| 2006/0200131 | A1 | 9/2006 | Chao et al. |
| 2007/0208344 | A1 | 9/2007 | Young |
| 2008/0015576 | A1 | 1/2008 | Whipple |
| 2008/0091213 | A1 | 4/2008 | Jackson |
| 2008/0125816 | A1 | 5/2008 | Jackson |
| 2008/0312701 | A1 | 12/2008 | Butters et al. |
| 2009/0005814 | A1 | 1/2009 | Miller et al. |
| 2009/0062866 | A1 | 3/2009 | Jackson |
| 2009/0163956 | A1 | 6/2009 | Biedermann et al. |
| 2009/0198280 | A1 | 8/2009 | Spratt et al. |
| 2009/0228053 | A1 | 9/2009 | Kolb et al. |
| 2009/0264941 | A1 | 10/2009 | Banouskou |
| 2010/0114171 | A1 | 5/2010 | Boachie-Adjei et al. |
| 2010/0125302 | A1 | 5/2010 | Hammill, Sr. et al. |
| 2010/0160977 | A1 | 6/2010 | Gephart et al. |
| 2010/0160978 | A1 | 6/2010 | Carbone |
| 2010/0204735 | A1 | 8/2010 | Gephart et al. |
| 2010/0305621 | A1 | 12/2010 | Wang et al. |
| 2011/0040336 | A1 | 2/2011 | Hammill et al. |
| 2012/0046699 | A1 | 2/2012 | Jones et al. |
| 2014/0012337 | A1 * | 1/2014 | Biedermann ........ A61B 17/844 606/328 |
| 2015/0196337 | A1 * | 7/2015 | Biedermann ...... A61B 17/7032 606/305 |
| 2016/0367295 | A1 * | 12/2016 | Biedermann ...... A61B 17/7085 |
| 2018/0028235 | A1 * | 2/2018 | Simpson ............ A61B 17/7017 |
| 2020/0054366 | A1 | 2/2020 | Ark et al. |

FOREIGN PATENT DOCUMENTS

| | | | |
|---|---|---|---|
| EP | 2052690 A1 | 4/2009 | |
| JP | 2004508130 A | 3/2004 | |
| JP | 2007526007 A | 9/2007 | |
| JP | 2009142655 A | 7/2009 | |
| WO | 2009015100 A2 | 1/2009 | |
| WO | 2010077284 A1 | 7/2010 | |

OTHER PUBLICATIONS

International Search Report and Written Opinion of the International Searching Authority mailed Mar. 5, 2011 from counterpart International Application No. PCT/US2011/048573.

Standard Specification and Test Methods for Metallic Medical Bone Screws; ASTM F543-07, ASTM International, 2007; pp. 1-20; www.astm.org.

Titanium Versalok Polyaxial Screw, Wright Medical Technology Inc., Apr. 1997; 1 page.

J.R. Chapman et al.; Factors Affecting the Pullout Strength of Cancellous Bone Screws, Journal of Biomechanical Engineering, Aug. 1996, vol. 118, pp. 391-398.

Amy W. L. Kwok, et al.; Insertional Torque and Pull-out Strengths of Conical and Cylindrical Pedicle Screws in Cadaveric Bone, Spine, 1996, vol. 21, No. 21, pp. 2429-2434.

Ferris M. Pfeiffer et al.; Comparison of Pullout Strength for Pedicle Screws of Different Designs, Spine, 2006, vol. 31, No. 23, 2006, pp. E867-E870.

Robert F. McLain et al.; Lumbar Pedicle Screw Salvage: Pullout Testing of Three Different Pedicle Screw Designs; Journal of Spinal Disorders, 1995, vol. 8, No. 1, pp. 62-68.

Oberg, E.; Jones, F.D.; Horton, H.L.; Ryffell, H.; Machinery's Handbook, 2000, Industrial Press, 26.sup.th Edition, pp. 1584-1591.

* cited by examiner

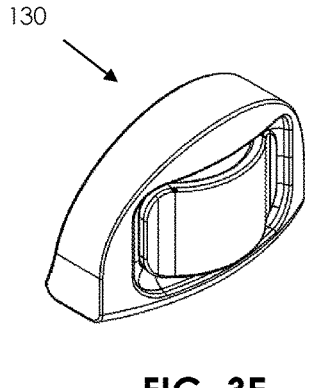
130
FIG. 3E
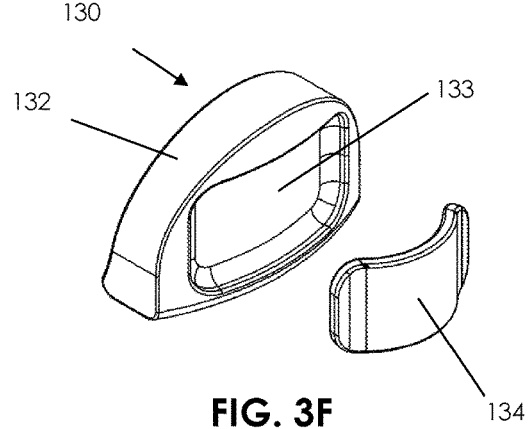
130
132    133
134
FIG. 3F
FIG. 3B
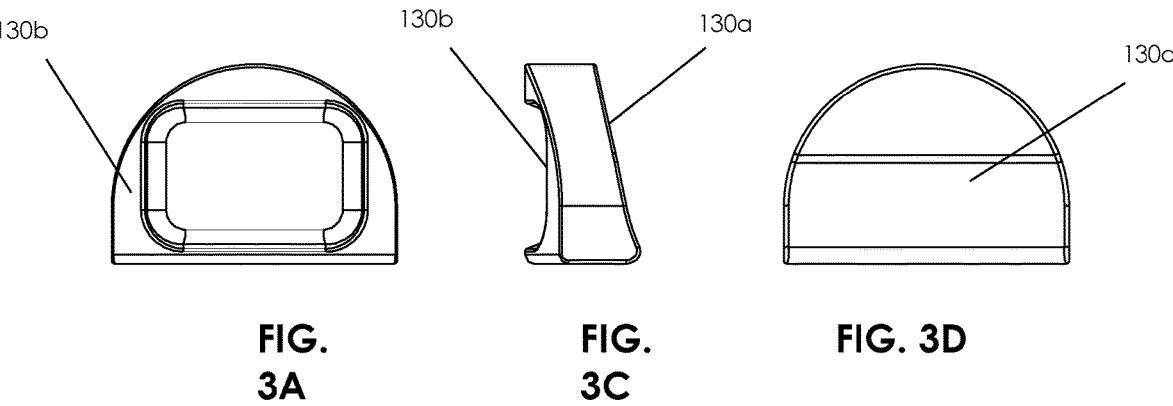
130b
130b    130a
130a
FIG. 3A    FIG. 3C    FIG. 3D

134

134b

134a

134b

134a

134a 134a     134b

134b

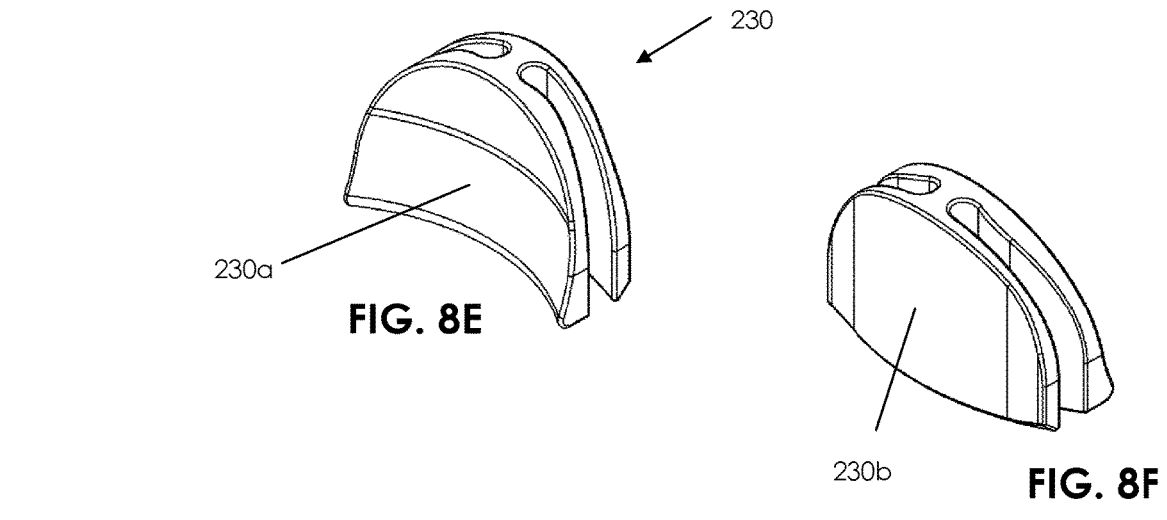
230
230a
FIG. 8E
230b
FIG. 8F
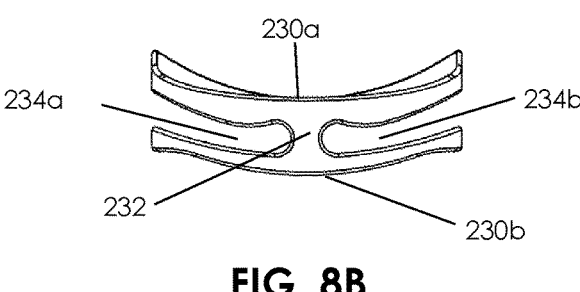
230a
234a
234b
232
230b
FIG. 8B
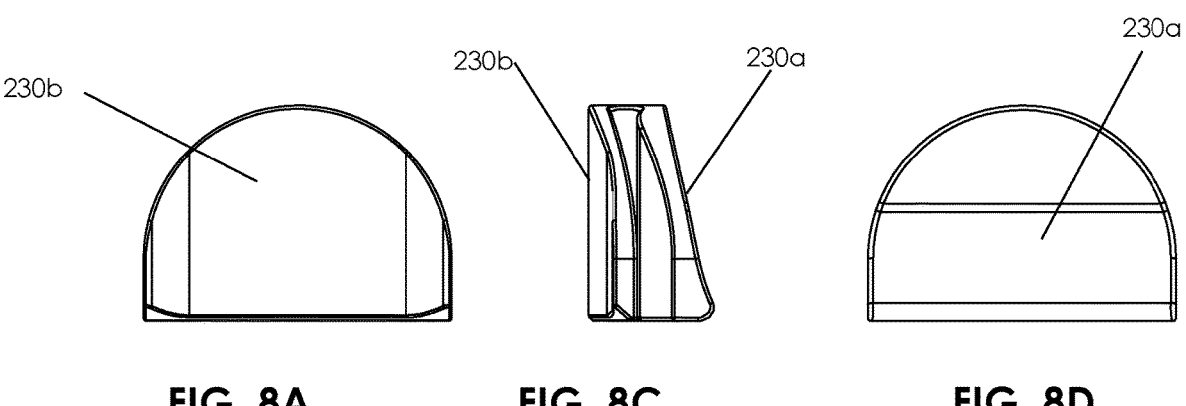
230b
230b
230a
230a
FIG. 8A          FIG. 8C          FIG. 8D

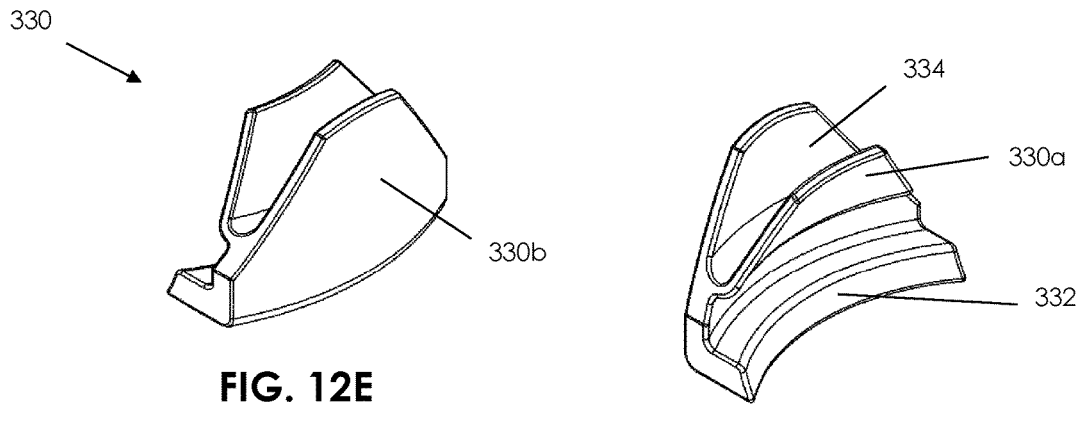
330
334
330a
332
330b
FIG. 12E
FIG. 12F
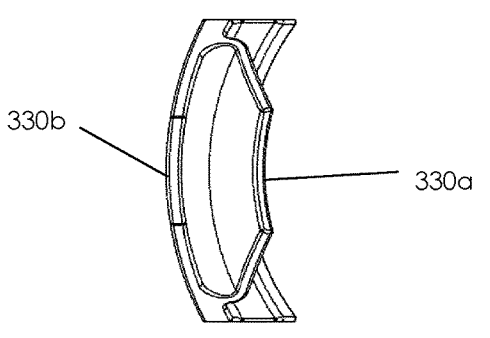
330b
330a
FIG. 12B
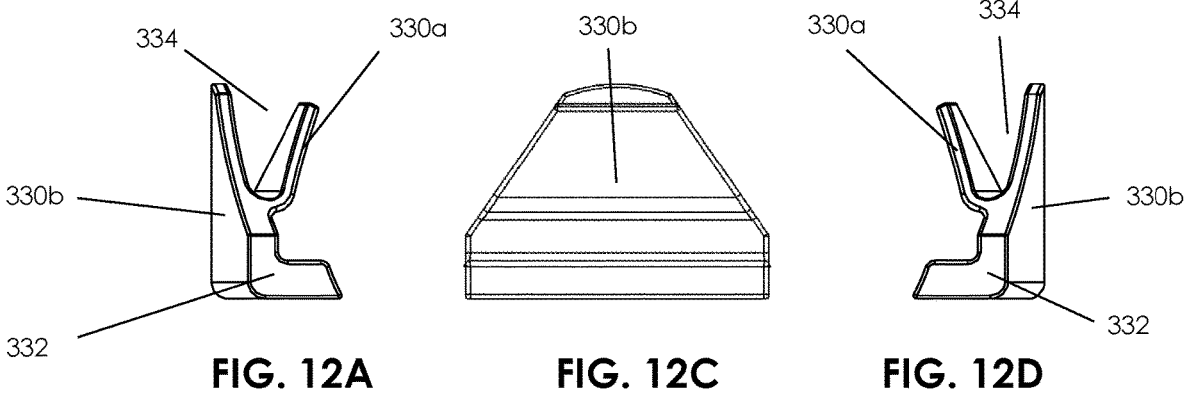
334     330a     330b     330a     334
330b     330b
332     332
FIG. 12A     FIG. 12C     FIG. 12D

SPINAL FIXATION SYSTEM

CROSS-REFERENCE TO RELATED APPLICATIONS

This application claims the benefit of the filing date of U.S. Provisional Patent Application No. 63/338,116 filed May 4, 2022, the disclosure of which is hereby incorporated herein by reference.

BACKGROUND OF THE DISCLOSURE

The present disclosure relates to spinal fixation devices and, more particularly, to pedicle screw fixation assemblies.

The spinal column is a complex system of bones and connective tissues that provides support for the body while protecting the spinal cord and nerves. The spinal column includes a series of vertebral bodies stacked on top of one another, each vertebral body including an inner or central portion of relatively weak cancellous bone and an outer portion of relatively strong cortical bone. Situated between each vertebral body is an intervertebral disc that cushions and dampens compressive forces exerted upon the spinal column, as well as maintains proper spacing of the bodies with respect to each other. A vertebral canal containing the spinal cord and nerves is located behind the vertebral bodies.

There are many types of spinal column disorders including scoliosis (abnormal lateral curvature of the spine), kyphosis (abnormal forward curvature of the spine, usually in the thoracic spine), excess lordosis (abnormal backward curvature of the spine, usually in the lumbar spine) and spondylolisthesis (forward displacement of one vertebra over another, usually in a lumbar or cervical spine), for example, that are caused by abnormalities, such as disease or trauma, and that are characterized by misalignment of the spinal column. When the spinal column is misaligned, one or more of the misaligned vertebral bodies can "pinch" or apply pressure to the underlying spinal cord and nerves, which often results in debilitating pain and diminished nerve function. For this reason, the forgoing conditions regularly require the imposition and/or maintenance of corrective forces on the spine in order to return the spine to its normal alignment.

A surgical technique, commonly referred to as spinal fixation, utilizes surgical implants for fusing together and/or mechanically immobilizing two or more vertebral bodies of the spinal column. Spinal fixation may also be used to alter the alignment of adjacent vertebral bodies relative to one another so as to change the overall alignment of the spinal column.

One common spinal fixation device utilizes spinal rods placed generally parallel to the spine and fixation devices, such as pedicle screw assemblies, interconnected between the spinal rods and selected portions of the spine. In some instances, the spinal rods can then be connected to each other via cross-connecting members to provide a more rigid support and alignment system.

Pedicle screw assemblies typically include a bone screw and a housing or coupling element for coupling the bone screw to the spinal rod. Pedicle screws generally come in two forms: a polyaxial pedicle screw (which allows the housing to freely rotate relative to the head of the screw) and a uniplanar pedicle screw (which restricts movement of the housing relative to the screw head to a single plane).

In both types of screws, unrestricted movement of the coupling element with respect to the screws is not preferable. This is often referred to as "flop," and can complicate the handling of the pedicle screw during a surgical procedure. Many different structures and techniques have been developed to combat this problem, but a need still exists for simple and easy assemblies that prevent the issue.

BRIEF SUMMARY OF THE DISCLOSURE

The present disclosure is directed to a polyaxial pedicle screw including a housing, a friction plug, an anvil, a bone screw member, and a compression ring or cap. The housing includes opposing arms, a collar at a bottom portion of the housing, a cutout, and a passage. The anvil is positioned in the passage. The bone screw member includes a head and a threaded shaft extending from the head along a shaft axis, wherein the head is configured to be positioned in the passage. The friction plug is positioned in the cutout, wherein the friction plug applies a force to the head. The compression ring or cap is positioned over the collar and the friction plug.

The friction plug includes a base member and a spring member positioned within the base member. An inner surface of the base member has a slight inward curve for engagement with the head of the bone screw member, and an outer surface of the base member has a slight outward curve for engagement with the cap. Further, an inner surface of the spring member has a slight inward curve, and an outer surface of the spring member has a slight outward curve for engagement with the compression ring or cap. The inner surfaces of the base member and spring member are generally aligned, as are the outer surfaces of the base member and spring member. When the inner surface of the base member is engaged by the head of the bone screw member, the spring member flexes inward and its relationship with the compression ring or cap causes a constant lateral force to be applied to the head of the bone member. The force applied to the head of the bone member restricts movement of the bone screw member within the housing.

In another embodiment, the friction plug includes an inner surface and an outer surface joined by a perpendicular support member. An inner surface has a slight inward curve for engagement with the head of the bone screw member, and an outer surface has a slight outward curve for engagement with the cap. The friction plug may be a bilateral leaf spring. When the inner surface is engaged by the head of the bone screw member, the outer surface flexes inward and its relationship with the compression ring or cap causes a force to be applied to the head of the bone member. The force applied to the head of the bone member restricts movement of the bone screw member within the housing. The head of the bone screw member may have a first portion and a second portion, wherein the second portion includes a surface texture, and the friction plug may include a surface texture for increased frictional engagement with the second portion.

Further, the inner surface and the outer surface of the friction plug may be joined at their respective centers by the perpendicular member. A first opening may be located adjacent to a first side of the perpendicular member between the inner surface and the outer surface, and a second space may be located adjacent a second side of the perpendicular member between the inner surface and the outer surface. Furthermore, the inner surface and the outer surface of the friction may have substantially semi-obround shapes, and a bottom portion of the inner and outer surfaces may be substantially planar.

In yet another embodiment, the friction plug includes an inner surface and an outer surface that are joined by a base member at a bottom portion of both the respective inner and outer surfaces. An inner surface has a slight inward curve for engagement with the head of the bone screw member, and an outer surface has a slight outward curve for engagement with the cap. Further, the base member has a slight inward curve for engagement with the head of the bone screw member. When the inner surface of the friction plug is engaged by the head of the bone screw member, the outer surface of the friction plug flexes inward and its relationship with the compression ring or cap causes a force to be applied to the head of the bone screw member. The force applied to the head of the bone screw member restricts movement of the bone screw member within the housing.

In yet another embodiment, the polyaxial pedicle screw includes a housing, a bone screw member, and an anvil. The housing includes opposing arms, a collar, and a passage. The bone screw member includes a head and a threaded shaft extending from the head along a shaft axis, wherein the head has a first portion and a second portion, the second portion having a surface texture. The anvil is positioned in the passage, wherein the anvil includes a spring element positioned in an inner portion of the anvil, wherein the spring element frictionally engages with the second portion of the head and provides a constant force to a top portion of the head. The spring element is a bilateral cantilevered spring positioned along a circumference of the inner portion of the anvil. In another embodiment, the spring element is comprised of multiple bilateral cantilevered springs individually positioned and spaced apart along a circumference of the inner portion of the anvil.

In yet another embodiment, a polyaxial pedicle screw includes a housing, a friction plug, an anvil, a bone screw member, and a compression ring or cap. The housing includes opposing arms, a collar at a bottom portion of the housing, a cutout, and a passage. The anvil is positioned in the passage. The bone screw member includes a head and a threaded shaft extending from the head along a shaft axis, wherein the head is configured to be positioned in the passage. The friction plug includes an inner surface and an outer surface joined by a perpendicular support member. The friction plug is positioned in the cutout and the inner surface is configured to engage the head and the outer surface is configured to engage the cap. The compression ring or cap is positioned over the collar and the friction plug. The friction plug may apply a force to the head, and the friction plug may be a bilateral leaf spring.

In yet another embodiment, a polyaxial pedicle screw includes a housing, a friction plug, an anvil, a bone screw member, and a compression ring or cap. The housing includes opposing arms, a collar at a bottom portion of the housing, a cutout, and a passage. The anvil is positioned in the passage. The bone screw member includes a head and a threaded shaft extending from the head along a shaft axis, wherein the head is configured to be positioned in the passage. The friction plug includes an inner surface and an outer surface joined by a perpendicular support member. The friction plug is positioned in the cutout and restricts movement of the bone screw member within the housing. The compression ring or cap is positioned over the collar and the friction plug. The friction plug may engage the head of the bone screw member and restrict movement of the head within the passage. Further, the friction plug may restrict polyaxial movement of the shaft relative to the shaft axis, and the friction plug may be a bilateral leaf spring.

BRIEF DESCRIPTION OF THE DRAWINGS

FIGS. 3A-3F are different views of a friction plug included in the pedicle screw of FIG. 1A.

FIGS. 8A-8F are different views of a friction plug included in the pedicle screw of FIG. 7.

FIGS. 12A-12F are different views of a friction plug included in the pedicle screw of FIG. 11.

FIG. 17A is a cross sectional exploded view of the pedicle screw of FIG. 15.

FIG. 17B is an enlarged view of a portion of FIG. 17A.

FIG. 18A is a cross sectional perspective view of the pedicle screw of FIG. 15.

FIG. 18B is an enlarged view of a portion of FIG. 18A.

DETAILED DESCRIPTION

Figures 1A, 1B:
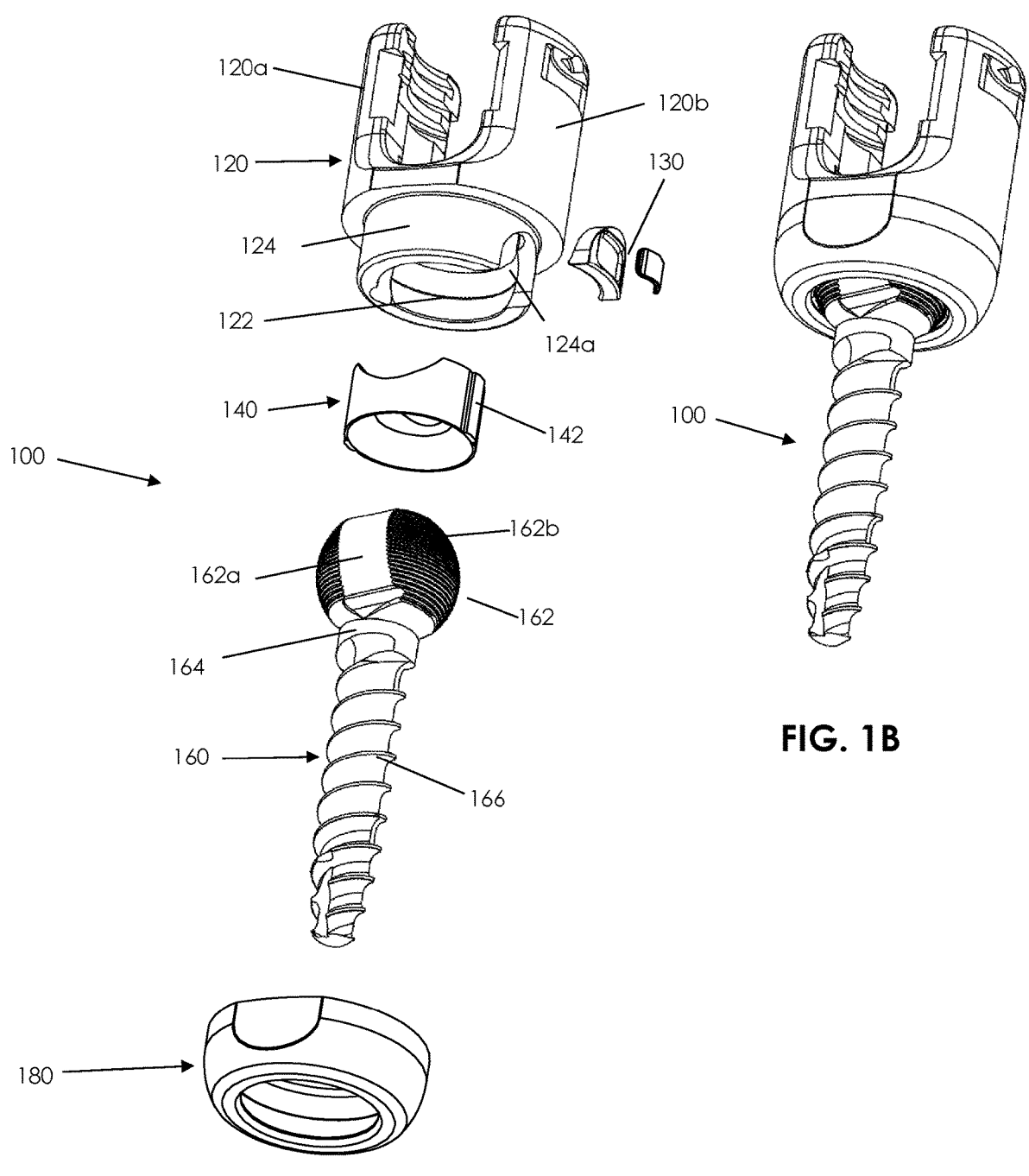
FIG. 1A is an exploded view of a pedicle screw according to an embodiment of the present disclosure.
FIG. 1B is a perspective view of the pedicle screw of FIG. 1A.
Figures 2A, 2B:
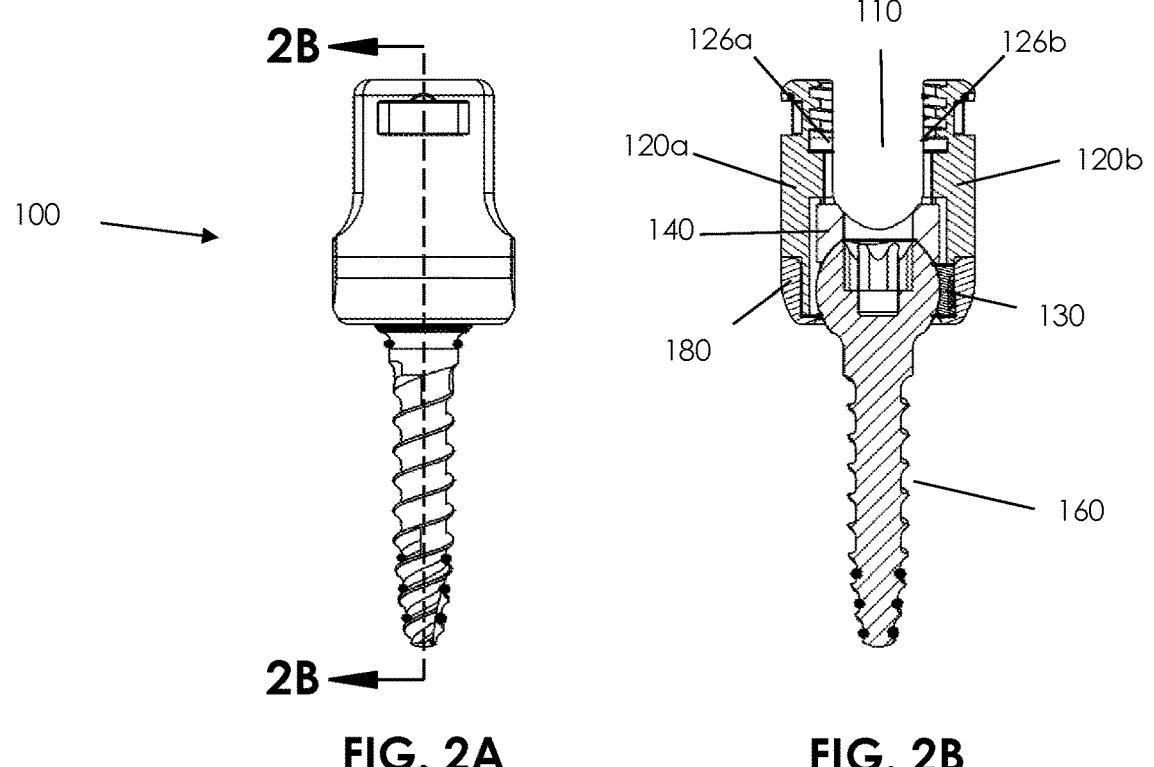
FIG. 2A is a side view of the pedicle screw of FIG. 1A.
FIG. 2B is a cross sectional view taken along line 2B-2B of FIG. 2A.
Figures 2C, 2D:
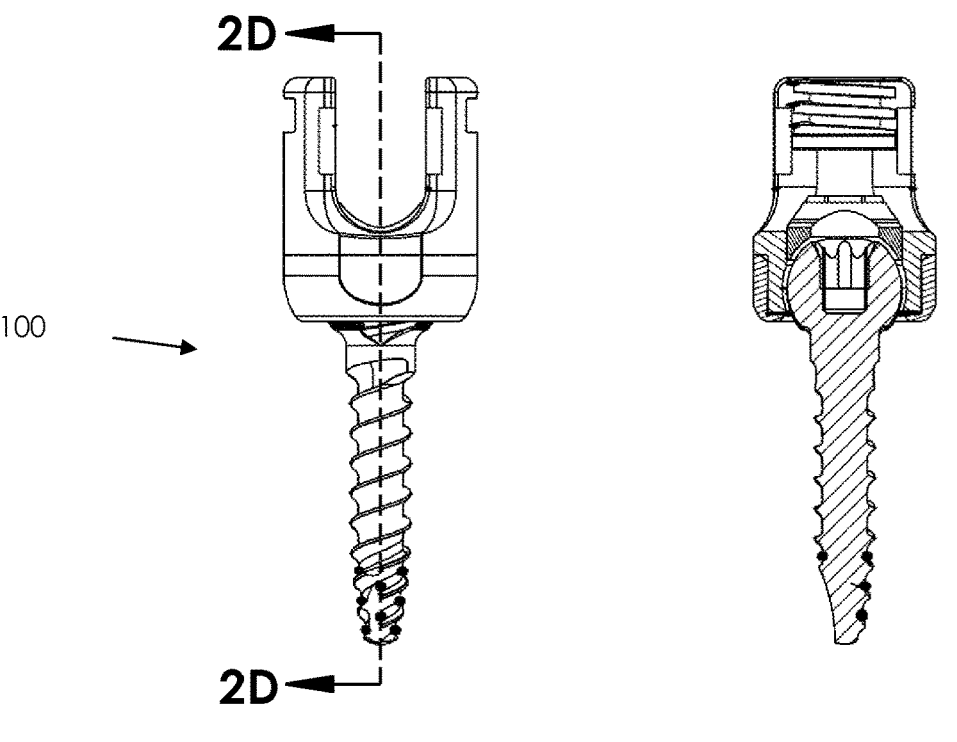
FIG. 2C is a front view of the pedicle screw of FIG. 1A.
FIG. 2D is a cross sectional view taken along line 2D-2D of FIG. 2C.
Figure 4E:
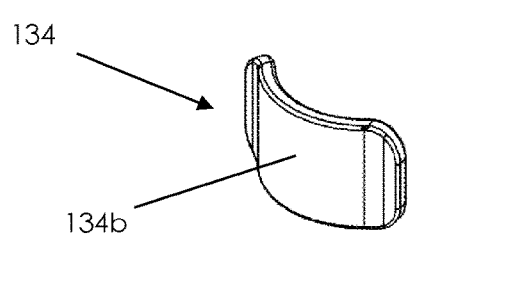
FIGS. 4A-4F are different views of a spring member included in the pedicle screw of FIG. 1A.
Figure 4F:
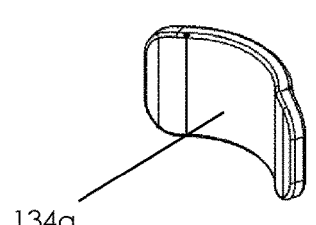
Figure 4B:
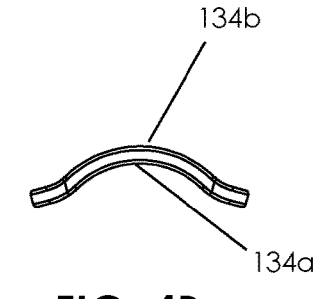
Figure 4A:
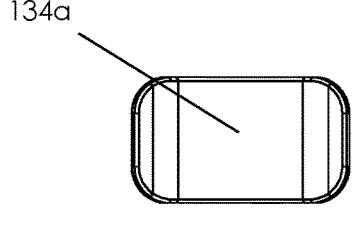
Figure 4C:
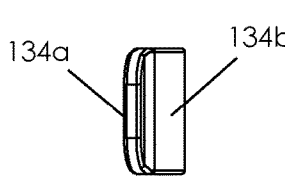
Figure 4D:
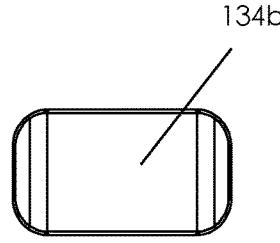

Particular embodiments of the present disclosure will be described herein with reference to the accompanying drawings. As shown in the drawings and as described throughout the following description, and as is traditional when referring to relative positioning on an object, the term "proximal" should be understood as referring to the portion of a structure that is closer to a clinician during proper use and the term "distal" should be understood as referring to the portion of a structure that is farther from the clinician during proper use. Also, as used herein, the terms "substantially," "generally," and "about" are intended to mean that slight deviations from absolute are included within the scope of the term so modified.

Referring to FIGS. 1A-2D, a polyaxial pedicle screw 100 in accordance with one embodiment of the present disclosure is shown. Polyaxial pedicle screw 100 includes a housing 120, a friction plug 130, an anvil 140, a bone screw member 160, and a compression ring or cap 180.

Housing 120 defines a passage 122 formed therethrough that permits the reception other elements of screw 100, along with a suitable driving instrument (not shown). The housing includes opposing arms 120a, 120b that define a U-shaped channel 110 therebetween. Housing 120 also includes a collar 124 extending from a bottom of the housing, which is shown having a smaller diameter than the diameter defined by the opposing arms 120a, 120b. Collar 124 is adapted to facilitate the securement of compression ring or cap 180 to the housing 120 once the bone screw member 160 is seated within passage 122. Collar 124 includes a cut out 124a that provides a recess for the reception of a portion of the bone screw member 160, namely a neck 164 (discussed further below). Housing 120 has one or more slots 126a, 126b positioned above a shoulder defined on an inner surface of the housing 120. The slots 126a, 126b extend continuously along opposing arms 120a, 120b.

Bone screw member 160 includes a head 162 and a threaded shaft 166. The head 162 includes a first portion 162a and a second portion 162b. First portion 162a is a cylindrical surface formed in the otherwise spherical head 162 (indeed second portion 162b is spherical) that enables the head 162 to fit through the bottom of housing 120 and ultimately into passage 122. Thus, in a position in which first portion 162a is aligned with passage 122, head 162 can be passed into the passage. In this position, neck 164 is received within cut out 124a. Thereafter, upon rotation of the head within the passage and movement of the neck from the cut out, second portion 162b maintains head 162 within housing 120. As shown, second portion 162b includes a surface texture in the form of serrations, which facilitate frictional engagement with other components of the assembly (e.g., anvil 140).

Prior to the insertion of head 162 in passage 122, anvil 140 is positioned in the passage. The placement of the head thereafter in fact captures the anvil within housing 120. The anvil 140 includes protuberances 142 on opposite sides of an outer surface of the anvil 140. These protuberances cooperate with slots (not shown) formed within passage 122 to prevent rotation of the anvil within the housing. Likewise, upper surfaces of the anvil abut the above-discussed shoulders formed with the passage to prevent further upward movement of anvil 140 within housing 120.

After the foregoing assembly steps, friction plug 130 is positioned in cutout 124a such that a portion of it abuts a portion of head 162 of bone screw member 160. This abutment creates a frictional relationship (aided by the surface texture of second portion 162b) created by the constant lateral force of the plug on the head 162. This precludes the aforementioned "flop" often seen with pedicle screws.

With all other components in place, compression ring or cap 180 may be slid over shaft 160 and affixed (such as by friction, threading, bayonet mount, gluing, ultrasonic or other welding or the like) to collar 124 of housing 120 to further secure friction plug 130 and bone screw member 160 to housing 120. The positioning of compression ring or cap 180 precludes bone screw member 160 from being positioned in a manner that would permit it to be removed from housing 120.

FIGS. 3A-3F depict friction plug 130 in more detail. As shown, friction plug 130 includes a base member 132 and a spring member 134 positioned within a recess 133 of base member 132. Friction plug 130 also includes an inner surface 130a and an outer surface 130b, with the inner surface 130a having a slight inward curve for engagement with head 162 and outer surface 130b having a slight outward curve for engagement with compression ring or cap 180.

Referring to FIGS. 4A-F, spring member 134 is a leaf spring that includes an inner surface 134a and an outer surface 134b. Inner surface 134a has a slight inward curve and outer surface 134b has a slight outward curve for engagement with compression ring or cap 180. Spring member 134 is positioned within recess 133 of base member 132 with inner surface 134a aligned with inner surface 130a, and outer surface 134b aligned with outer surface 130b. Outer surface 134b frictionally engages with compression ring or cap 180 to provide a constant lateral force and cause inner surface 130a to engage head 162.

Figures 5A, 5B, 6A, 6B:
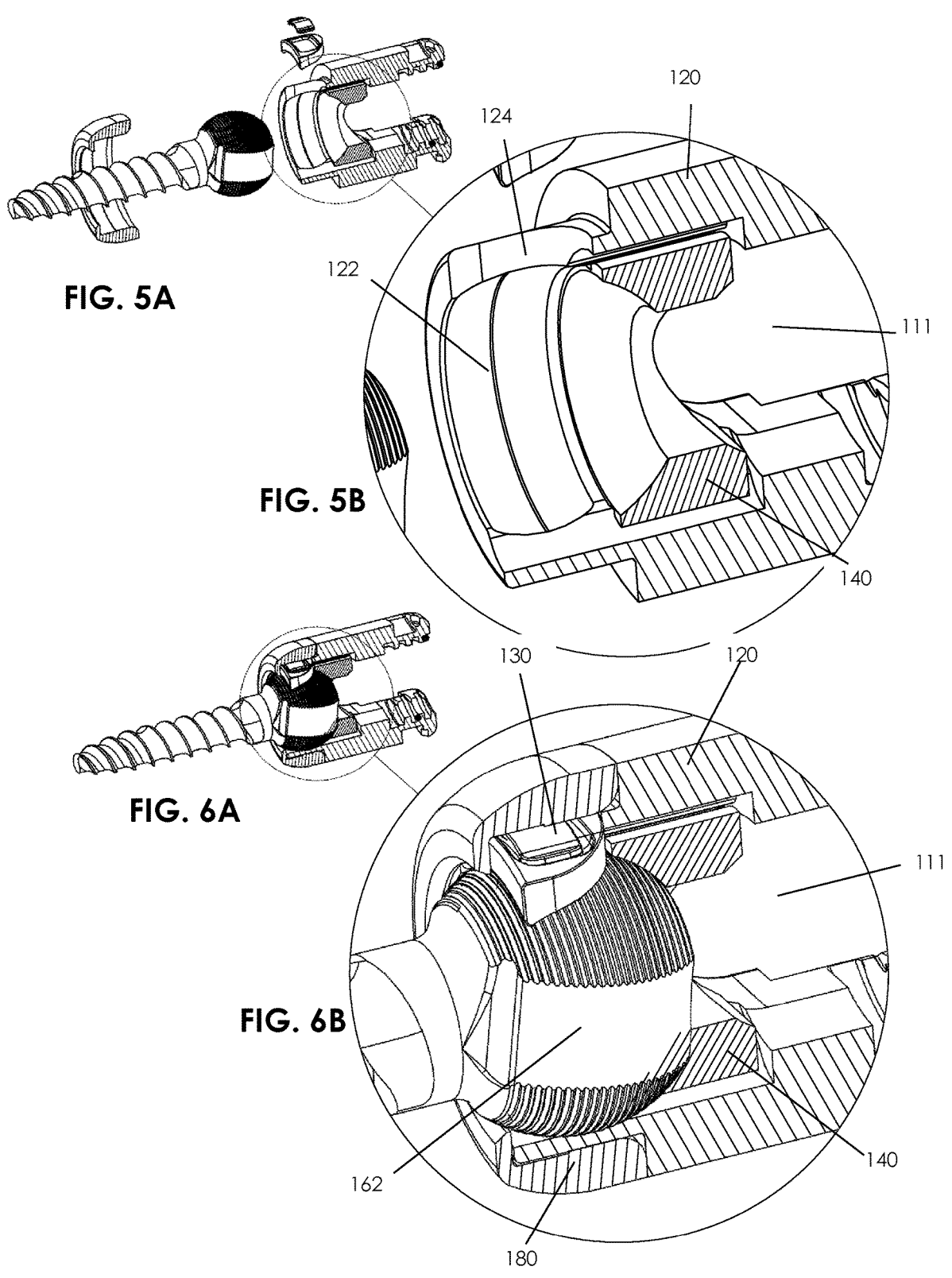
FIG. 5A is a cross sectional exploded view of the pedicle screw of FIG. 1A.
FIG. 5B is an enlarged view of a portion of FIG. 5A.
FIG. 6A is a cross sectional perspective view of the pedicle screw of FIG. 1A.
FIG. 6B is an enlarged view of a portion of FIG. 6A.
Figure 7:
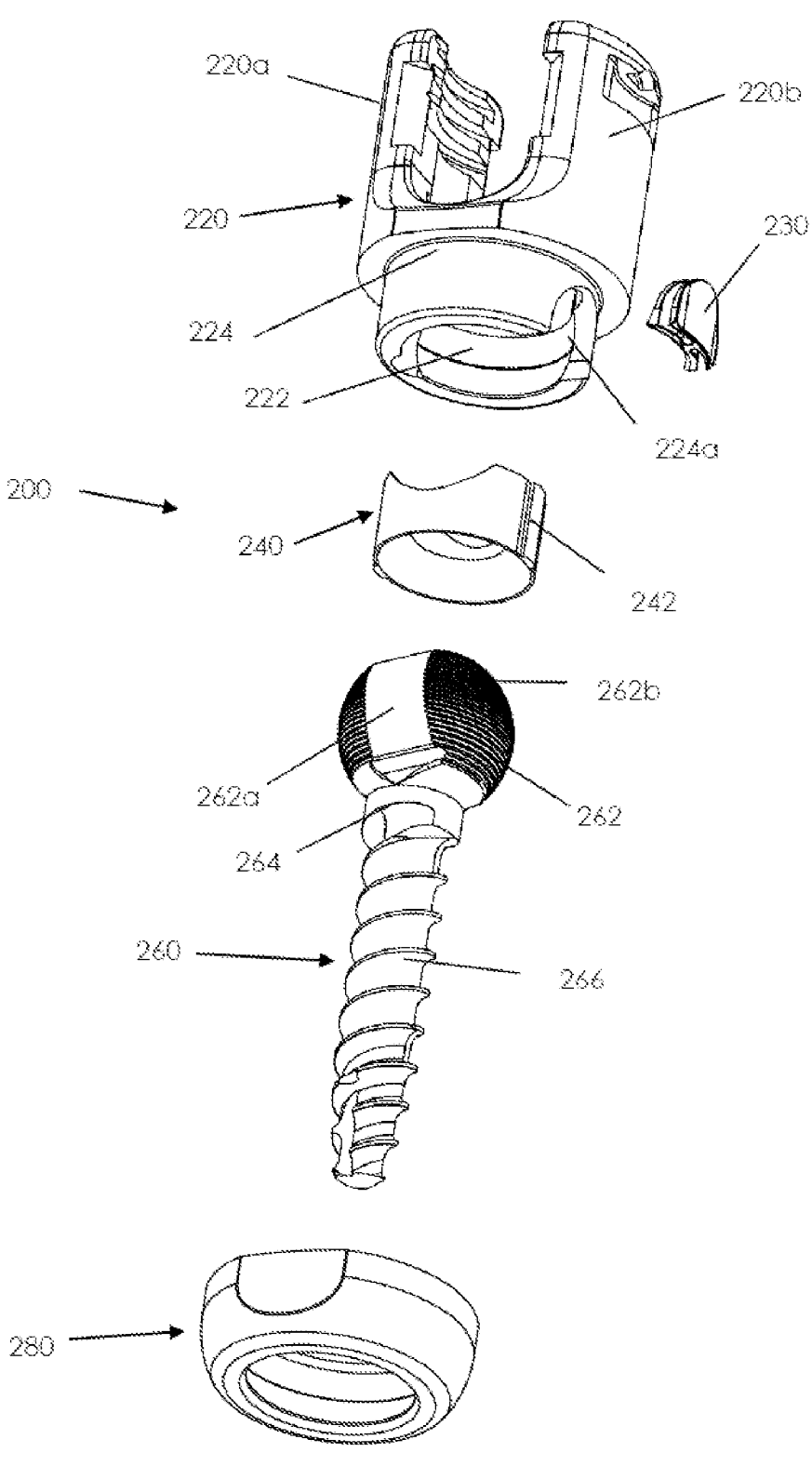
FIG. 7 is an exploded view of a pedicle screw according to another embodiment of the present disclosure.

The interrelationships among the various components discussed above can be seen in the cross-sectional views of FIGS. 5A-6B. Specifically, FIG. 5B includes an enlarged view of anvil 140 positioned in housing 120 prior to the bone screw member 160 and friction plug 130 being positioned in housing 120. FIG. 6B, on the other hand, includes an enlarged view of the fully assembled construct. As shown, inner surface 130a of friction plug 130 is positioned to engage with head 162, and outer surface 130b is positioned to engage compression ring or cap 180 which further secures each component within housing 120.

In the fully assembled state, friction plug 130 frictionally engages with head 162 to provide a constant lateral force. Spring member 134, when positioned within recess 133 of base member 132, flexes inward and its relationship with compression ring or cap 180 causes the constant force to ultimately be applied to head 162 by base member 132 which restricts movement of bone screw member 160 within housing 120.

Another embodiment pedicle screw 200 is shown in FIGS. 7-10 with like reference numerals being utilized in connection with similar components to that of pedicle screw 100, but within the 200-series of numbers. For instance, pedicle screw 200 includes a housing 220, a friction plug 230, an anvil 240, a bone screw member 260, and a compression ring or cap 280. In fact, the below discussion is focused on the only component that significantly differs from that of pedicle screw 100—friction plug 230.

FIGS. 8A-F depict friction plug 230 in more detail. As shown, friction plug 230 is a bilateral leaf spring which includes an inner surface 230a and an outer surface 230b, with inner surface 230a having a slight inward curve for engagement with head 262 and outer surface 230b having a slight outward curve for engagement with compression ring or cap 280. Inner surface 230a and outer surface 230b are joined at about their centers by a perpendicular support member 232. Adjacent to either side of support member 232 and in-between inner and outer surfaces 230*a*, 230*b* are open spaces 234*a*, 234*b*.

Figures 9A, 9B, 10A, 10B:
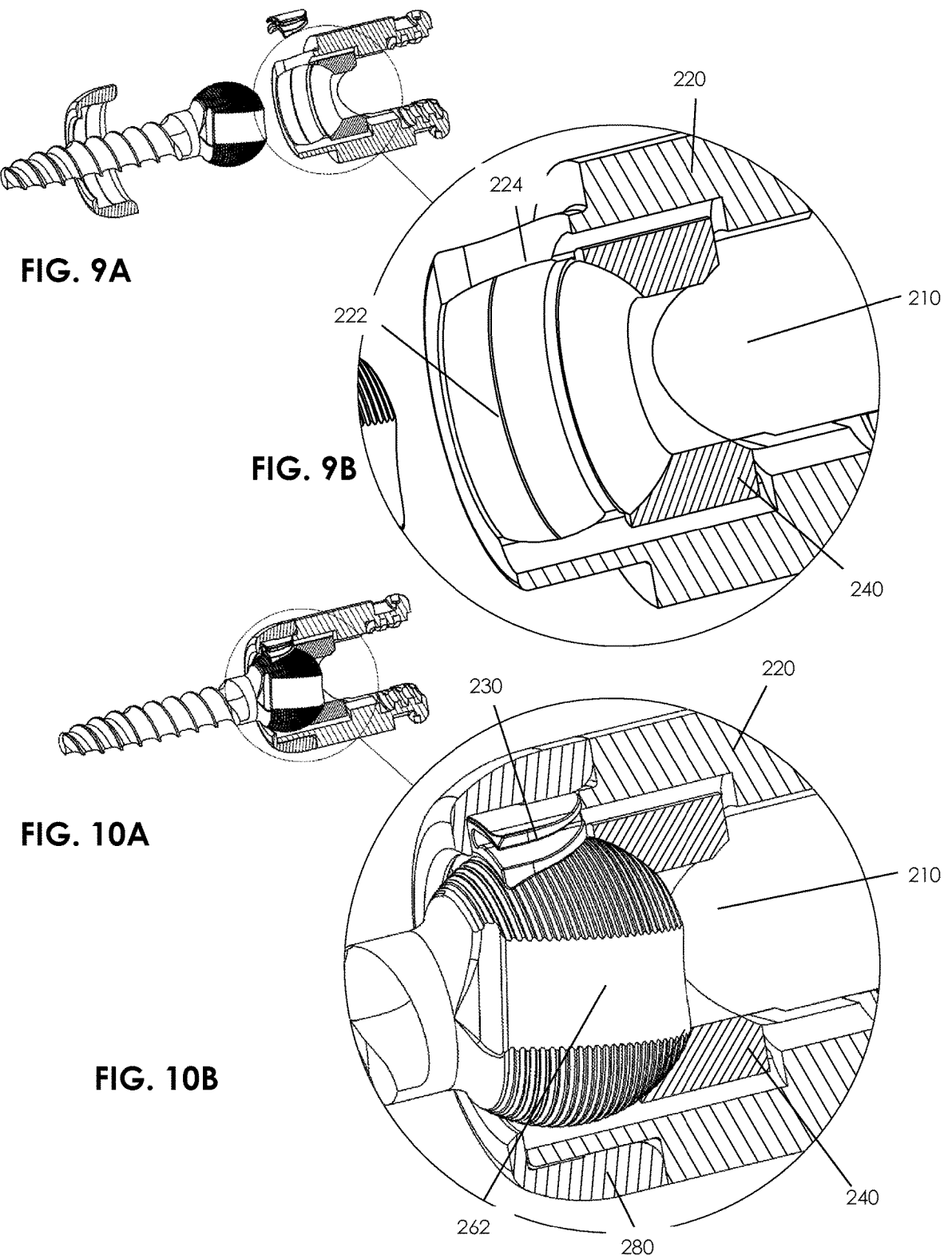
FIG. 9A is a cross sectional exploded view of the pedicle screw of FIG. 7.
FIG. 9B is an enlarged view of a portion of FIG. 9A.
FIG. 10A is a cross sectional perspective view of the pedicle screw of FIG. 7.
FIG. 10B is an enlarged view of a portion of FIG. 10A.
Figure 11:
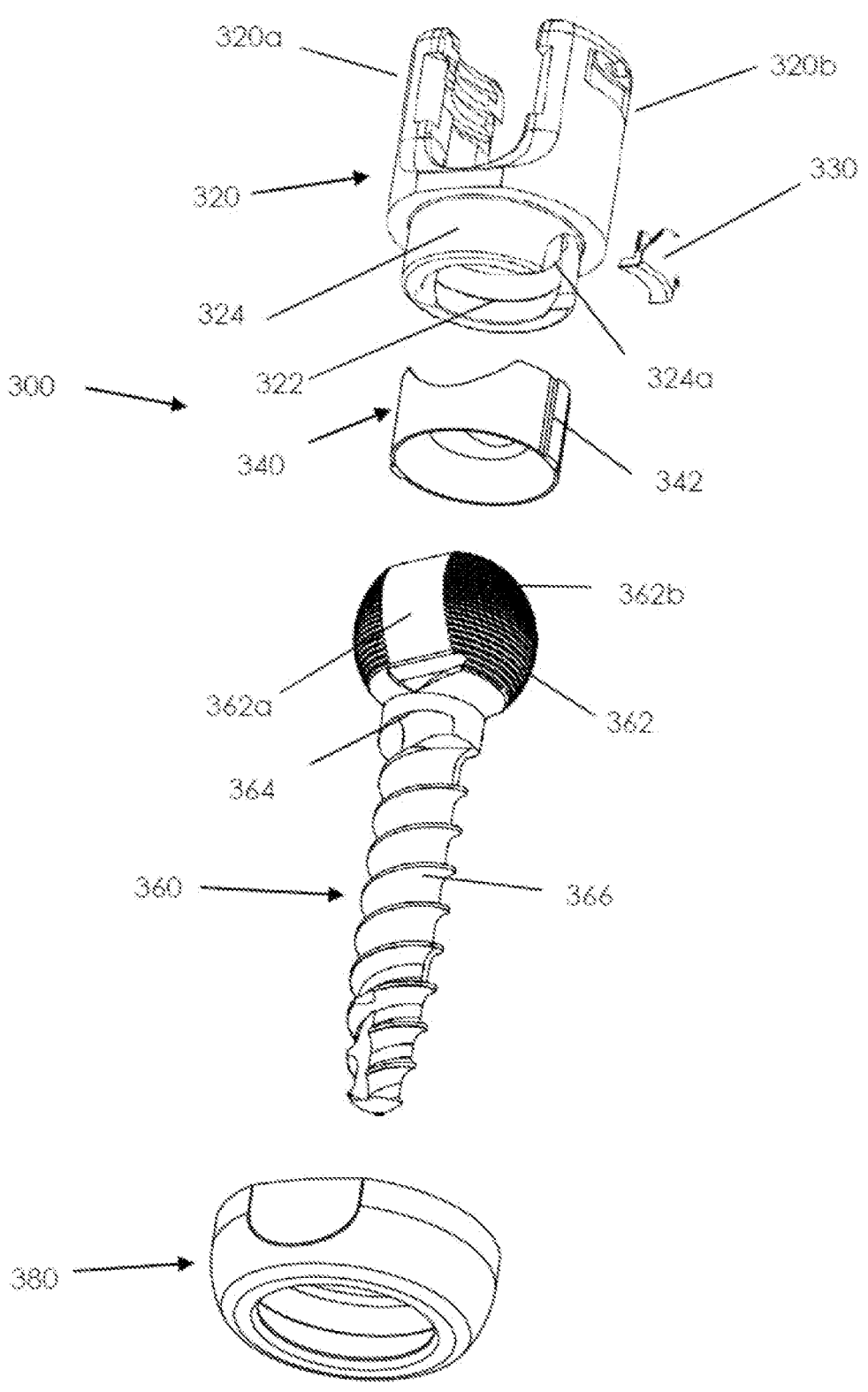
FIG. 11 is an exploded view of a pedicle screw according to another embodiment of the present disclosure.

The interrelationships among the various components discussed above can be seen in an enlarged view of the fully assembled construct in cross-sectional view FIG. 10B. As shown, inner surface 230*a* of friction plug 230 is positioned to engage with head 262, and outer surface 230*b* is positioned to engage with compression ring or cap 280 which further secures each component within housing 220.

In the fully assembled state, friction plug 230 frictionally engages with head 262 to provide a constant lateral force. Outer surface 230*b* flexes outward when inner surface 230*a* is engaged by head 262. Outer surface 230*b* relationship with compression ring or cap 280 causes constant force to ultimately be applied to head 262 by inner surface 230*a* which restricts movement of bone screw member 260 within the housing 220.

Another embodiment pedicle screw 300 is shown in FIGS. 11-14 with like reference numerals being utilized in connection with similar components to that of pedicle screw 100 and 200, but within the 300-series of numbers. For instance, pedicle screw 300 includes a housing 320, a friction plug 330, an anvil 340, a bone screw member 360, and a compression ring or cap 380. In fact, the below discussion is focused on the only component that significantly differs from that of pedicle screw 100 and 200-friction plug 330.

FIGS. 12A-F depict friction plug 330 in more detail. As shown, friction plug 330 is bilateral leaf spring which includes an inner surface 330*a* and an outer surface 330*b*, with inner surface 330*a* having a slight inward curve for engagement with head 362 and outer surface 330*b* having a slight outward curve for engagement with compression ring or cap 380. Inner surface 330*a* and outer surface 330*b* are joined at about their respective bottom portions by a base member 332, with base member 332 having a slight inward curve for engagement with head 362. In-between inner and outer surfaces 330*a*, 330*b* is open space 334.

Figures 13A, 13B, 14A, 14B:
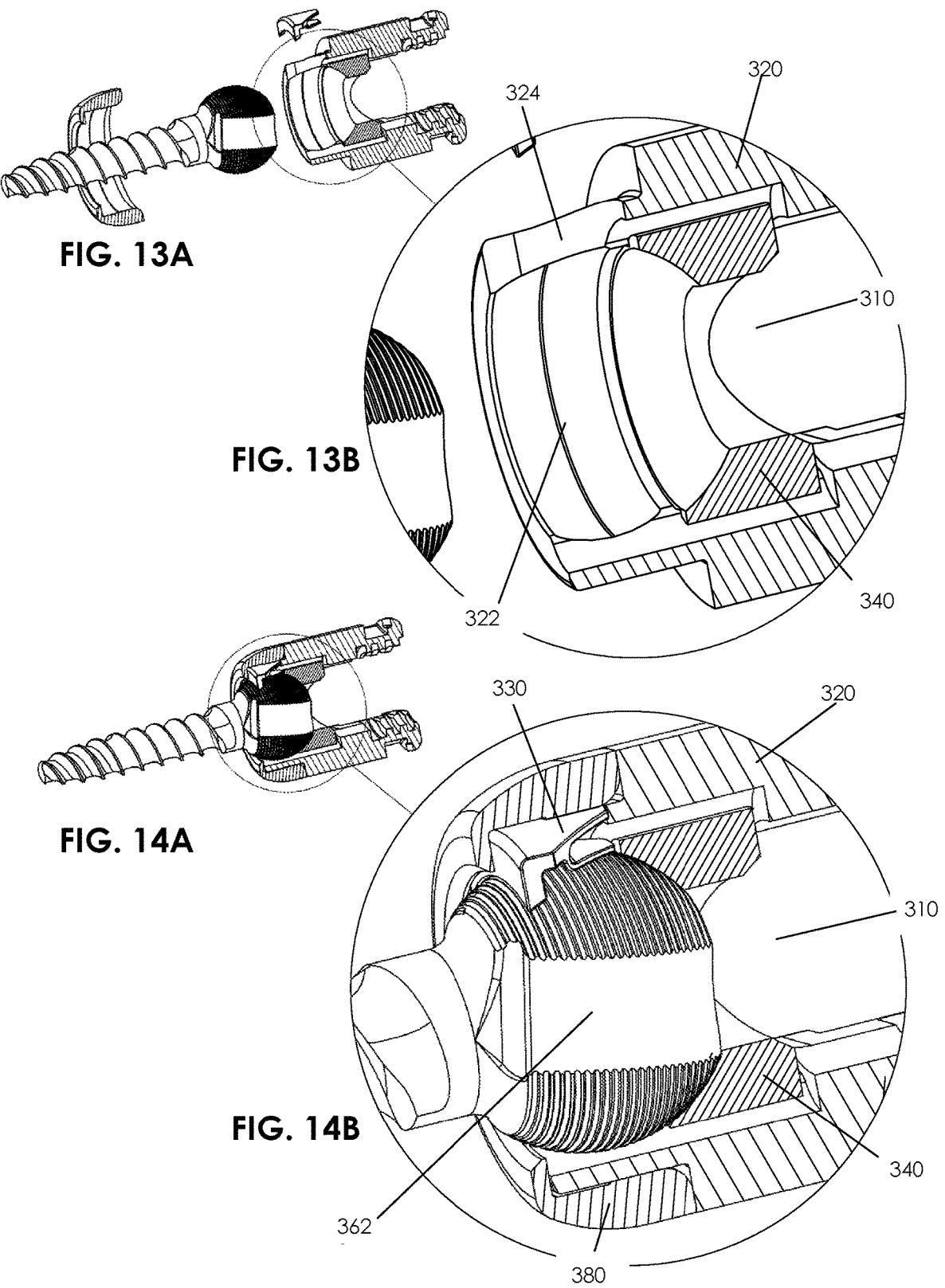
FIG. 13A is a cross sectional exploded view of the pedicle screw of FIG. 11.
FIG. 13B is an enlarged view of a portion of FIG. 13A.
FIG. 14A is a cross sectional perspective view of the pedicle screw of FIG. 11.
FIG. 14B is an enlarged view of a portion of FIG. 14A.
Figure 15:
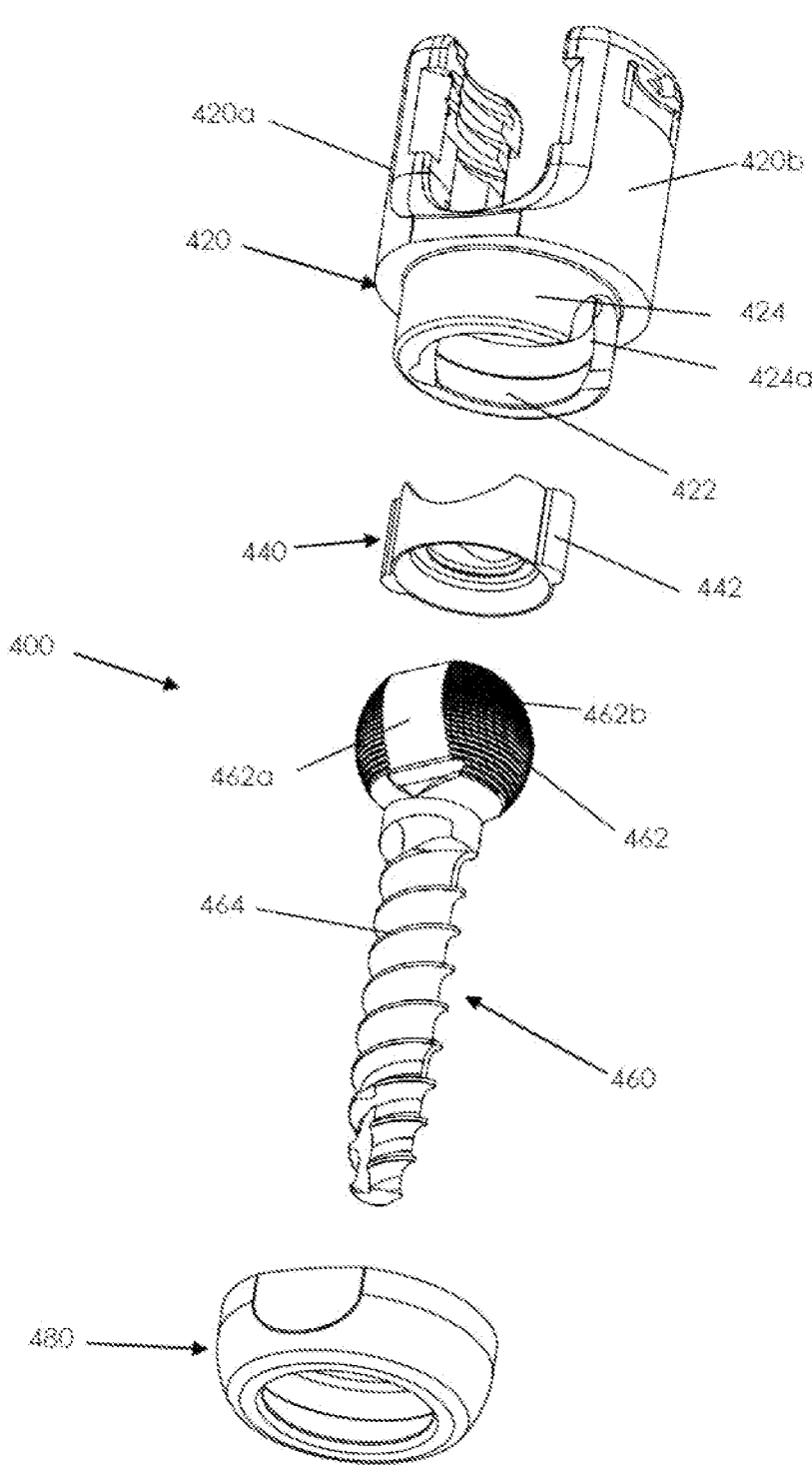
FIG. 15 is an exploded view of a pedicle screw according to another embodiment of the present disclosure.

The interrelationships among the various components discussed above can be seen in an enlarged view of the fully assembled construct in cross-sectional view FIG. 14B. As shown, inner surface 330*a* and base member 332 of friction plug 330 is positioned to engage with head 362, and outer surface 330*b* is positioned to engage with compression ring or cap 380 which further secures each component within housing 320.

In the fully assembled state, friction plug 330 frictionally engages with head 362 to provide a constant lateral force. Outer surface 330*b* flexes outward when inner surface 330*a* is engaged by head 362. Outer surface 330*b* relationship with compression ring or cap 380 causes constant force to ultimately be applied to head 362 by inner surface 330*a* which restricts movement of bone screw member 360 within the housing 320.

Another embodiment pedicle screw 400 is shown in FIGS. 15-18 with like reference numbers being utilized in connection with similar components of that of pedicle screws 100, 200, and 300, but within the 400-series of numbers. Pedicle screw 400, however, does not include a friction plug but rather a modified anvil. For instance, pedicle screw 400 includes a housing 420, an anvil 440, a bone screw member 460, and a compression ring or cap 480. The below discussion is focused on the only component that significantly differs from that of pedicle screws 100, 200, and 300—anvil 440.

Figure 16A:
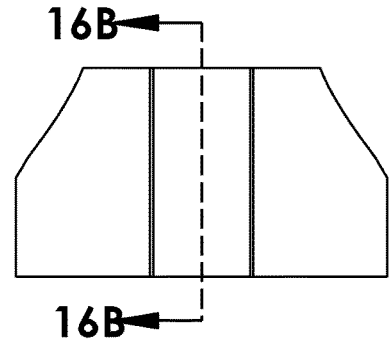
FIG. 16A is a side view of an anvil of the pedicle screw of FIG. 15.
Figure 16B:
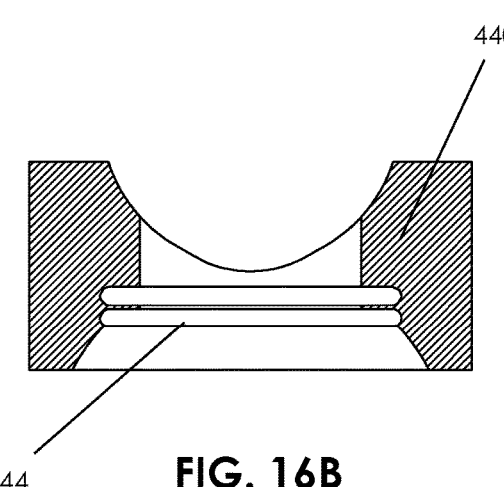
FIG. 16B is a cross sectional view taken along 16B-16B of FIG. 16A.
Figure 16C:
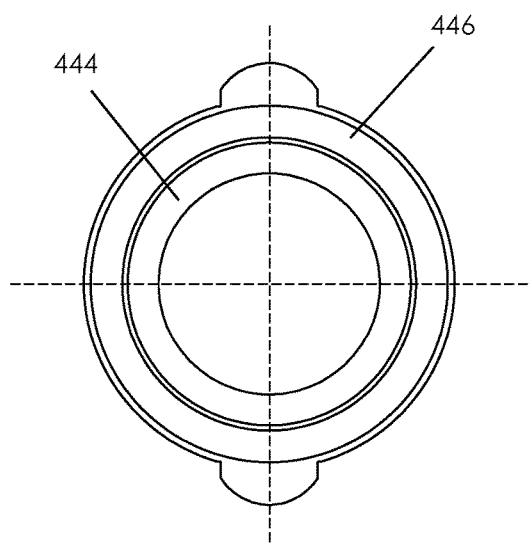
FIG. 16C is a bottom view of the anvil of FIG. 16A.
Figure 19:
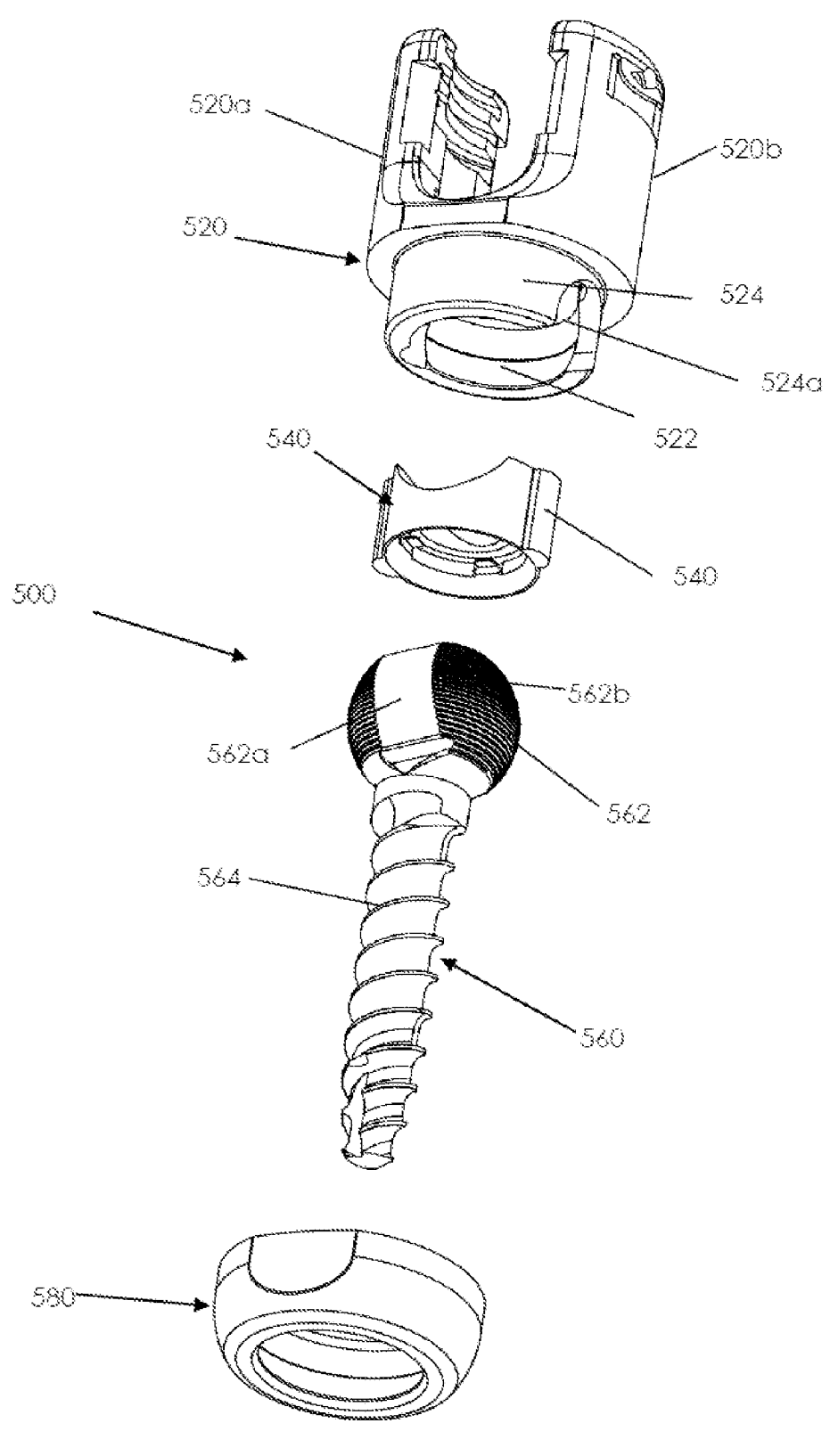
FIG. 19 is an exploded view of a pedicle screw according to another embodiment of the present disclosure.

FIGS. 16A-C depict anvil 440 in more detail. Anvil 440 includes a spring element 444 positioned within an inner surface 446 that fully encompasses the circumference of anvil 440. Spring element 444 is a bilateral cantilevered spring as shown.

The interrelationships among the various components discussed above can be seen in the cross-sectional views of FIGS. 17A-18B. FIG. 17B includes an enlarged view of anvil 440 positioned in housing 420 prior to bone screw member 460 being positioned in housing 420.

Figures 17A, 17B, 18A, 18B:
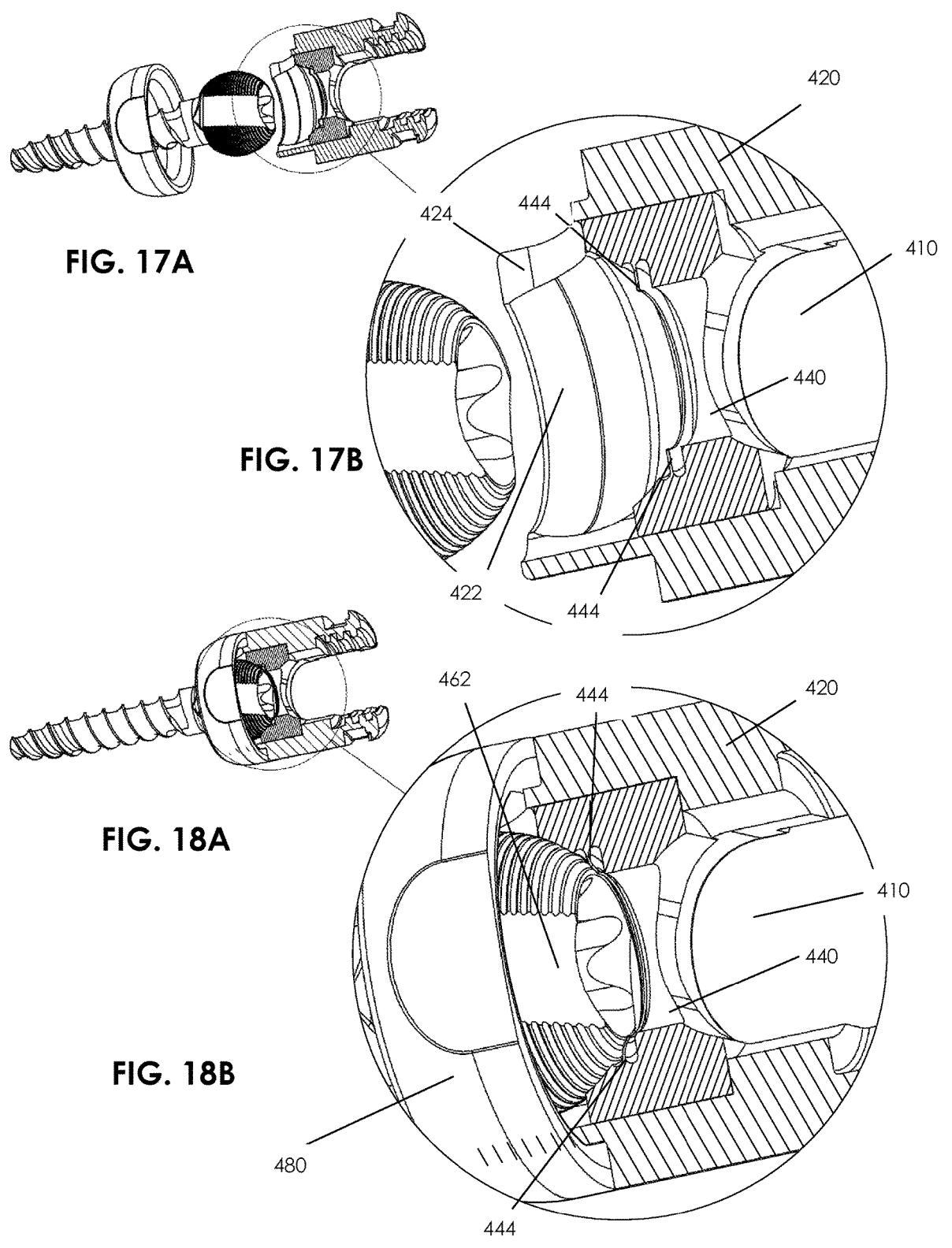

FIG. 18B, on the other hand, includes an enlarged view of the fully assembled construct. As shown, spring element 444 of anvil 440 is positioned to engage with head 462 and compression ring or cap 480 further secures each component within housing 420.

In the fully assembled state, anvil 440 frictionally engages with head 462 to provide a constant force. When bone screw member 460 is positioned within anvil 440, spring element 444 engages a second portion 462*b* of the head 462 causing the spring element 444 to flex upward. The upward flex of the spring element 444 causes the constant force to ultimately be applied to head 462 by anvil 440 which restricts movement of bone screw member 460 within the housing 420.

Another embodiment pedicle screw 500 is shown in FIGS. 19-22 with like reference numerals being utilized in connection with similar components to that of pedicle screws 100, 200, 300 and 400, but within the 500-series of numbers. Pedicle screw 500, similar to pedicle screw 400, does not include a friction plug but rather a modified anvil. Pedicle screw 500 includes a housing 520, an anvil 540, a bone screw member 560, and a compression ring or cap 580. The below discussion is focused on the only component that significantly differs from that of pedicle screws 100, 200, 300, and 400—anvil 540.

Figure 20A:
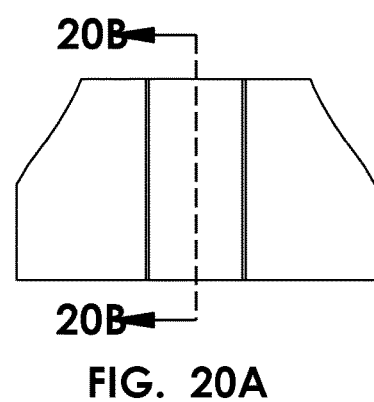
FIG. 20A is a side view of an anvil of the pedicle screw of FIG. 19.
Figure 20B:
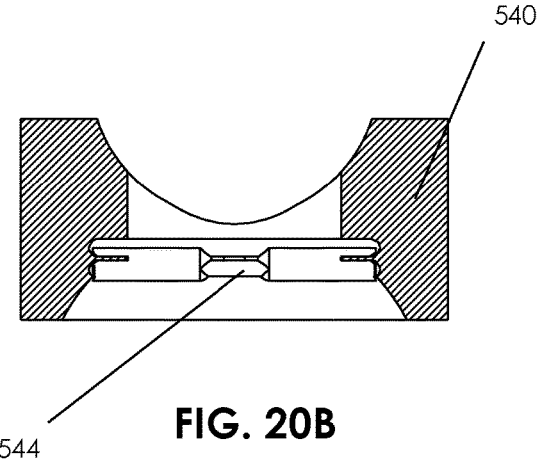
FIG. 20B is a cross sectional view taken along 20B-20B of FIG. 20A.
Figure 20C:
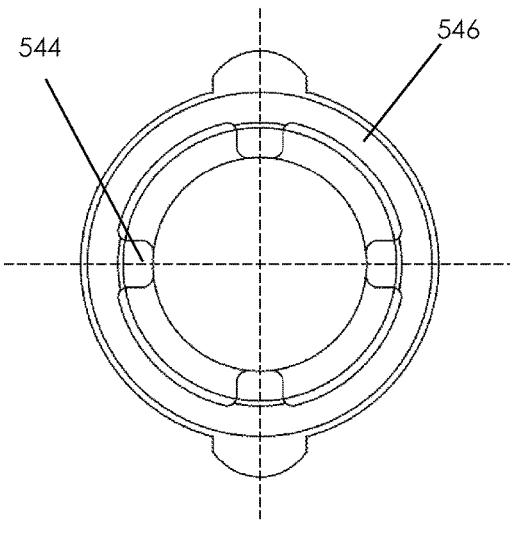
FIG. 20C is a bottom view of the anvil of FIG. 20A.

FIGS. 20A-C depict anvil 540 in more detail. Anvil 540 includes spring elements 544 positioned within an inner surface 546 that fully encompasses the circumference of anvil 540. Spring elements 544 are bilateral cantilevered springs as shown.

The interrelationships among the various components discussed above can be seen in the cross-sectional views of FIGS. 21A-22B. FIG. 21B includes an enlarged view of the anvil 540 positioned in housing 520 prior to bone screw member 560 being positioned in housing 520.

Figures 21A, 21B, 22A, 22B:
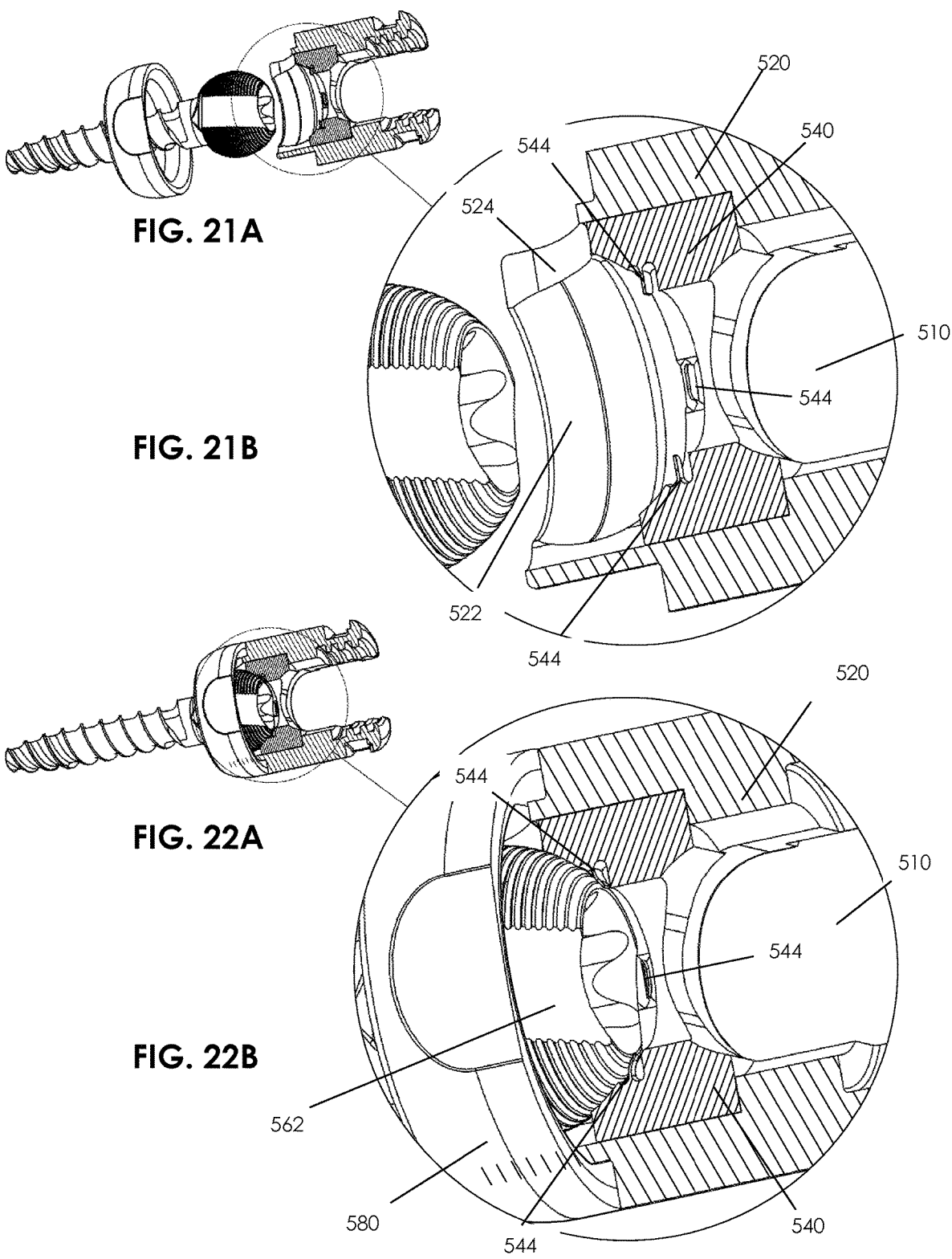
FIG. 21A is a cross sectional exploded view of the pedicle screw of FIG. 19.
FIG. 21B is an enlarged view of a portion of FIG. 21A.
FIG. 22A is a cross sectional perspective view of the pedicle screw of FIG. 19.
FIG. 22B is an enlarged view of a portion of FIG. 22A.

FIG. 22B, on the other hand, includes an enlarged view of the fully assembled construct. As shown, spring elements 544 of anvil 540 are positioned to engage head 562 and compression ring or cap 580 further secures each component within housing 520.

In the fully assembled state, anvil 540 frictionally engages with head to provide a constant force. When bone screw member 560 is positioned within anvil 540, spring elements 544 engages a second portion 562*b* of the head 562 causing the spring elements 544 to flex upward. The upward flex of the spring element 544 causes the constant force to ultimately be applied to head 562 by anvil 540 which restricts movement of bone screw member 560 within the housing 520.

As can be appreciated, any portion of any of the presently disclosed polyaxial pedicle screws can be formed of titanium, titanium alloy, stainless steel, cobalt chrome, or other metal or polymeric materials. In this regard, it is also appreciated that utilizing a combination of compatible materials in the screw assembly may be advantageous. Thus, it is contemplated that the housing could be made of a harder or stiffer material such as cobalt chrome, while the screw and anvil and set screw may be made of another, compatible material such as titanium or titanium alloy. Further, components of any of the presently disclosed embodiments may be press fit, staked, pinned, or welded together.

Alternative embodiments are also contemplated herein. For instance, the second portion of the bone screw member may include a surface texture in the form of knurling, while the friction plug can include a similar texture. It is also contemplated that different features of different embodiments can be utilized together, such as a design in which the spring elements are included both in the anvil and the friction plug.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A polyaxial pedicle screw comprising:
a housing including opposing arms, a collar at a bottom portion of the housing, a cutout through a portion of the collar, and a passage extending through the housing;
an anvil positioned in the passage;
a bone screw member including a head and a threaded shaft extending from the head along a shaft axis, wherein the head is configured to be positioned in the passage;
a friction plug positioned in the cutout, wherein the friction plug includes an inner surface and an outer surface joined by a perpendicular support member, and wherein the friction plug applies a force to the head; and
a cap positioned over the collar and the friction plug,
wherein the inner surface has an inward curve for engagement with the head and the outer surface has an outward curve for engagement with the cap.

2. The polyaxial pedicle screw of claim 1, wherein the friction plug is a bilateral leaf spring.

3. The polyaxial pedicle screw of claim 1, wherein the head has a first portion and a second portion, wherein the second portion includes a surface texture.

4. The polyaxial pedicle screw of claim 3, wherein the friction plug has a surface texture for increased frictional engagement with the second portion of the head.

5. The polyaxial pedicle screw of claim 1, wherein the inner surface and the outer surface are joined at their respective centers by the perpendicular support member.

6. The polyaxial pedicle screw of claim 1, wherein a first open space is located adjacent a first side of the perpendicular support member between the inner surface and the outer surface.

7. The polyaxial pedicle screw of claim 6, wherein a second open space is located adjacent a second side of the perpendicular support member between the inner surface and the outer surface.

8. The polyaxial pedicle screw of claim 1, wherein the outer surface flexes outward in a direction opposite the head.

9. The polyaxial pedicle screw of claim 1, wherein the inner surface restricts polyaxial movement of bone screw member within the housing.

10. The polyaxial pedicle screw of claim 1, wherein the inner surface has a concave shape and the outer surfaces has a convex shape.

11. The polyaxial pedicle screw of claim 10, wherein a bottom portion of the inner and outer surfaces are substantially planar.

12. A polyaxial pedicle screw comprising:
a housing including opposing arms, a collar at a bottom portion of the housing, a cutout through a portion of the collar, and a passage extending through the housing;
an anvil positioned in the passage;
a bone screw member including a head and a threaded shaft extending from the head along a shaft axis, wherein the head is configured to be positioned in the passage;
a cap positioned over the collar and the cutout; and
a friction plug including an inner surface and an outer surface joined by a perpendicular support member, wherein the friction plug is positioned in the cutout and the inner surface is configured to engage the head and the outer surface is configured to engage the cap.

13. The polyaxial pedicle screw of claim 12, wherein the friction plug applies a force to the head.

14. The polyaxial pedicle screw of claim 13, wherein the friction plug is a bilateral leaf spring.

15. A polyaxial pedicle screw comprising:
a housing including opposing arms, a collar at a bottom portion of the housing, a cutout through a portion of the collar and a passage extending through the housing;
an anvil positioned in the passage;
a bone screw member including a head and a threaded shaft extending from the head along a shaft axis, wherein the head is configured to be positioned in the passage;
a friction plug including an inner surface and an outer surface joined by a perpendicular support member, wherein the friction plug is positioned in the cutout and restricts movement of the bone screw member within the housing; and
a cap positioned over the collar and the friction plug,
wherein the friction plug engages the head of the bone screw member and the friction plug restricts movement of the head within the passage,
wherein the friction plug restricts polyaxial movement of the shaft relative to the shaft axis, and
wherein the friction plug is a bilateral leaf spring.

* * * * *